United States Patent
Yamaguchi (10) Patent No.: US 8,134,692 B2
(45) Date of Patent: Mar. 13, 2012

(54) FOG DETECTOR AND METHOD OF PLACING DETECTOR IN VEHICLE

(75) Inventor: Kazuhiko Yamaguchi, Gifu (JP)

(73) Assignee: Denso Corporation, Kariya (JP)

( * ) Notice: Subject to any disclaimer, the term of this patent is extended or adjusted under 35 U.S.C. 154(b) by 532 days.

(21) Appl. No.: 12/277,426

(22) Filed: Nov. 25, 2008

(65) Prior Publication Data
US 2009/0138210 A1    May 28, 2009

(30) Foreign Application Priority Data
Nov. 26, 2007    (JP) .................................. 2007-304675

(51) Int. Cl.
*G01C 3/08*    (2006.01)

(52) U.S. Cl. ........ 356/5.01; 356/4.01; 356/4.1; 356/5.1; 356/5.15

(58) Field of Classification Search ......... 356/3.01–28.5
See application file for complete search history.

(56) References Cited

U.S. PATENT DOCUMENTS

| | | | |
|---|---|---|---|
| 3,578,211 A * | 5/1971 | Coapman et al. ............... | 222/56 |
| 4,931,767 A | 6/1990 | Albrecht et al. | |
| 5,349,267 A * | 9/1994 | Brassier et al. ................. | 315/82 |
| 6,108,084 A | 8/2000 | Winner | |
| 6,377,167 B1 | 4/2002 | Juds et al. | |
| 2007/0090311 A1 | 4/2007 | Pallaro | |

FOREIGN PATENT DOCUMENTS

| | | | |
|---|---|---|---|
| DE | 195 30 289 | | 2/1997 |
| DE | 196 29 713 | | 1/1998 |
| DE | 19629713 | * | 1/1998 |
| JP | 6-099772 | | 4/1994 |
| JP | 06-043587 | | 6/1994 |
| JP | 2001-511530 | | 8/2001 |
| JP | 2007-114193 | | 5/2007 |
| WO | WO 99/05661 | | 2/1999 |

OTHER PUBLICATIONS

Japanese Office Action dated Oct. 13, 2009, issued in corresponding Japanese Application No. 2007-304675, with English translation.
Extended European Search Report dated Feb. 19, 2010, issued in corresponding European Application No. 08020446.4-2204.

* cited by examiner

*Primary Examiner* — Thomas Tarcza
*Assistant Examiner* — Luke Ratcliffe
(74) *Attorney, Agent, or Firm* — Nixon & Vanderhye P.C.

(57) ABSTRACT

A light emitting element and a light receiving element is placed in such a manner that the light axis of a light emitting element constructing a light emitting circuit and the light axis of a light receiving element constructing a light receiving circuit cross each other. The light pathway length R1, R2 of both the light waves are determined in such a manner that the object light, the light waves via the object pathway, are delayed by π/2 in phase from the reflected light, i.e. relative to light waves via the reflected light pathway. A synchronous detector selects signals having the same phase as the object light from receive signals provided from the light receiving circuit. Accordingly, the fog detector can detect the object light without being influenced of the reflected light, which allows a determination processing device to accurately determine the density of fog.

12 Claims, 6 Drawing Sheets

FOG DETECTOR AND METHOD OF PLACING DETECTOR IN VEHICLE

CROSS REFERENCE TO RELATED APPLICATION

The present application relates to and incorporates by reference Japanese Patent application No. 2007-304675 filed on Nov. 26, 2007.

BACKGROUND OF THE INVENTION

1. Technical Field

The present invention relates to a fog detector mounted to a vehicle, and a method of placing the fog detector.

2. Background Technology

Fog detectors have been known. The fog detectors are designed to detect the density of fog by emitting infrared radiation and receiving reflected infrared radiation reflected by particles of the fog (backscattered light).

One type of the fog detectors can perform a stable detection despite any undesirable surrounding environment. This fog detector comprises a light emitting element that reflected infrared radiation and a light receiving element that receives the emitted infrared radiation. The light emitting element and the light receiving element are placed in such a manner that the light axes of the elements cross each other. The light receiving element is designed to receive only the backscattered light reflected within a predetermined area of the detector. Such fog detector is disclosed, for example, in Japanese Unexamined Patent Publication No. H06-99772.

Retrofitting the fog detector in the vehicle interior has been proposed, instead of installing it to the vehicle bumper at the beginning during manufacturing, or even installing the fog detector in the vehicle interior, for the purpose of easy maintenance, at the beginning during manufacturing has been proposed.

However, because the fog detector installed in the vehicle interior is designed to emit and receive the infrared radiation through a window glass (a front glass or a rear glass), it receives not only backscattered light from the fog but also reflected light from a window glass, particularly when the window glass is obscured with dust, drops of water, or the like.

Because the amount of the reflected light from the window glass is larger than that of the backscattered light from the fog, the backscattered light is buried in the reflected light, inducing the inaccurate detection of the backscattered light.

To solve such problem the window glass has to be separated into two sections, one for passing the emitting light and the other for passing the receiving light so as not to receive the reflected light from the window glass, or in order to maintain the glass surface to accurately reflect the light constantly.

However, the former case requires a particular kind of glass to be used for a front glass or a rear glass, and the latter case requires the glass surface to be maintained constantly. Therefore, both cases are indeed unpractical.

SUMMARY OF THE INVENTION

It is therefore an object of the present invention to provide a fog detector that can perform accurate detection of the density of fog, even under the presence of reflected light from the window glass. Another object of the present invention is to provide a placement method of the fog detector.

The present invention has been invented to achieve the above-mentioned object. A fog detector in a first aspect of the invention is placed in a vehicle interior that is segregated from an exterior of the vehicle by a translucent protective wall. The fog detector comprises an emitting/receiving device, which includes a light emitting element and a light receiving element. The light emitting element and the light receiving element are placed in such a manner that the light axes of the elements cross each other.

The fog detector also comprises a signal processing device and a determination processing device. The signal processing device that provides a transmission signal having predetermined frequency to the light emitting element for emitting the light waves also performs a synchronous detection of a received signal corresponding to the received light waves provided from the light receiving element so as to extract a signal corresponding to a reflected light waves reflected at the crossing point of the light axes, wherein the synchronous detection is performed using a reference signal having the same frequency as the transmission signal and the same phase as the reflected light waves reflected at the crossing point of the light axes. The determination processing device determines whether or not fog exists based on results of the synchronous detection performed by the signal processing device.

In such constructed fog detector, the synchronous detection can detect reflected light having the same phase as reflected light from the crossing point of the light axes, among reflected light having the same frequency as the transmitted signals. Therefore, placement of the fog detector in such a manner that the phase of reflected light from the protective wall is dissimilar to the phase of the reference waves allows the reflected light from the crossing point of the light axes (the backscattered light from the fog) to be detected, with no influence of the reflected light from the protective wall (the ideal difference of the phases is $(2n-1)\pi/2$). Consequently, the fog detector can perform an accurate determination of the fog density.

It is desirable to construct the fog detector as a second aspect of the invention: that is, the light emitting element and the light receiving element have such a characteristic that a light receiving angle $2\theta_1$ of the light receiving element and a spread dimension $2\theta_2$ of the emitted light from the light emitting element satisfy the following formula. In the formula, the symbol "x" refers to a linear distance between an element placing surface and the crossing point of the light axes. The light emitting element and the light receiving element are placed on the element placing surface. The symbol "$\phi_1$" prefers to a light axis angle of the light receiving element relative to the element placing surface, and the symbol "$\phi_2$" refers to a light axis angle of the light emitting element relative to the element placing surface. Further, the symbol "y" refers to a placement distance between the light emitting element and the light receiving element.

$$y < \frac{2x}{\tan(\phi_1 + \theta_1)} + \frac{2x}{\tan(\phi_2 + \theta_2)} \quad (1)$$

$$y > \frac{x}{\tan(\phi_1 + \theta_1)} + \frac{x}{\tan(\phi_2 + \theta_2)} \quad (2)$$

That is, the light receiving element receives the backscattered light from the fog that is present in the crossing area of the beams. This area has a spread dimension of $2\theta_1$ about the light axis of the light receiving element (received light axis) and also having a spread (angular) dimension of $2\theta_2$ about the light axis of the light emitting element (emitted light axis) where they cross each other. The formula (1) demonstrates a condition that causes the length of a pathway of the light (light pathway length) emitted from the light emitting element and reaches the light receiving element through reflection by the fog present in the cross area to become less than two times of the wavelength of the light wave (see, FIG. 6(a)). The formula (2) demonstrates a condition that causes some of the light pathway length of the light emitted from the light emitting element and reaches the light receiving element through reflection by the fog present in the cross area to surely become equal to the wavelength of the light wave (see, FIG. 6(b)).

A third aspect of the invention discloses that the wavelength of transmission signals λ can be determined to satisfy the following formula under the condition: that is, the emitting/receiving device is placed in such a manner that the light axes of the emitting/receiving device pass through the protective wall, presenting the crossing point of the light axes at an exterior of the vehicle, and that a difference distance between the light pathway length of light waves round-tripping the crossing point of the light axes and the light pathway length of light waves reflecting at the protective wall is ΔR.

$$\Delta R = \lambda/4 \quad (3)$$

That is, if the placement position of the emitting/receiving device has been determined, an arrangement of the wavelength of the transmission signals determined by the formula (3) allows the synchronous detection to sufficiently remove the influence of light waves reflected by the protective wall.

A fog detector according to a fourth aspect of the invention is placed in a vehicle interior that is segregated from an exterior by a translucent protective wall. The fog detector comprises an emitting/receiving device that includes a light emitting element and a light receiving element. The light emitting element and the light receiving element are placed in such a manner that the light axes of the elements cross each other.

The fog detector also comprises a signal processing device that provides transmission signals having predetermined pulse width to the light emitting element. The signal processing device detects the signal level of receive signals provided from the light receiving element. The fog detector further comprises a determination processing device that determines the fog density based on results of detection detected by the signal processing device. The results of detection are detected at a timing delayed for the time that is required for the light waves to reach the light receiving element through the reflection at the crossing point of the light axes after emission from the light emitting element.

A fog detector constructed in this manner can detect the backscattered light reflected from the crossing point without being influenced by the light waves reflected at the protective wall. It can be done by means of a placement of the emitting/receiving device and an arrangement of the pulse width of the transmission signals in such a manner that the timing to receive the reflected wave from the protective wall and the timing to receive the backscattered light from the crossing point do not overlap each other. Consequently, the fog detector can perform an accurate determination of the fog density.

A fifth aspect of the invention discloses that the pulse width "Tp" of the transmission signals should satisfy the following formula, in which "c" indicates the speed of light, under the condition below. That is, the emitting/receiving device is placed in such a manner that the light axes of the emitting/receiving device pass through the protective wall, presenting the crossing point of the light axes at an exterior of the vehicle, and that the difference distance between the light pathway length of light waves round-tripping the crossing point of the light axes and the light pathway length of light waves reflecting at the protective wall becomes ΔR.

$$\Delta R/c > Tp \quad (4)$$

Accordingly, the fog detector can avoid the overlap between the backscattered light from the fog and the reflected light from the protective wall, which sufficiently removes influence of the reflected light.

A sixth aspect of the invention discloses a placement method of the fog detector disclosed in the first and second aspects of the invention. The method includes placing the emitting/receiving device in such a manner that the light axes of the emitting/receiving device pass through the protective wall, presenting the crossing point of the light axes at an exterior of the vehicle. The method also includes satisfying the following formula to determine the placement position of the emitting/receiving device. In this formula, the symbol "ΔR" refers to the difference distance between the light pathway length round-tripping the crossing point of the light axes and the light pathway length reflecting at the protective wall. Also, the symbol "λ" refers to the wavelength of the transmission signals.

$$\Delta R = \lambda/4 \quad (5)$$

That is, when the wavelength λ of the transmission signals has been fixed, the synchronous detection can remove influence of the reflected light waves from the protective wall, by determining the placement position of the emitting/receiving device by following the formula (5).

A seventh aspect of the invention relates to the fog detector disclosed in the fourth aspect of the invention. The method includes placing the emitting/receiving device in such a manner that the light axes of the emitting/receiving device pass through the protective wall, presenting the crossing point of the light axes at an exterior of the vehicle. The method also includes satisfying the following formula to determine the placement position of the emitting/receiving device. In the formula, the symbol "ΔR" refers to the difference distance between the light pathway length of light waves round-tripping the crossing point of the light axes and the light pathway length of light waves reflecting at the protective wall. The symbol "c" refers to the speed of light, and "Tp" refers to the pulse width of the transmission signals.

$$\Delta R/c > Tp \quad (6)$$

That is, when the pulse width Tp of the transmission signals has been fixed, the determination of the placement position of the emitting/receiving device according to the formula (6) can avoid the overlap between the backscattered light from the fog and the reflected light from the protective wall, and can sufficiently remove any influence of the reflected light.

An eighth aspect of the invention discloses a method that the protective wall should be provided with a wiper for removing drops of water adhered to the outer surface of the protective wall.

A ninth aspect of the invention discloses a method that the protective wall should be a front glass or a rear glass. The emitting/receiving device can be placed inside a headlight that is equipped with a wiper.

DETAILED DESCRIPTION OF PREFERRED EMBODIMENTS

A preferred embodiment of the present invention will be described hereinafter referring to the drawings.

First Embodiment

Figure 1:
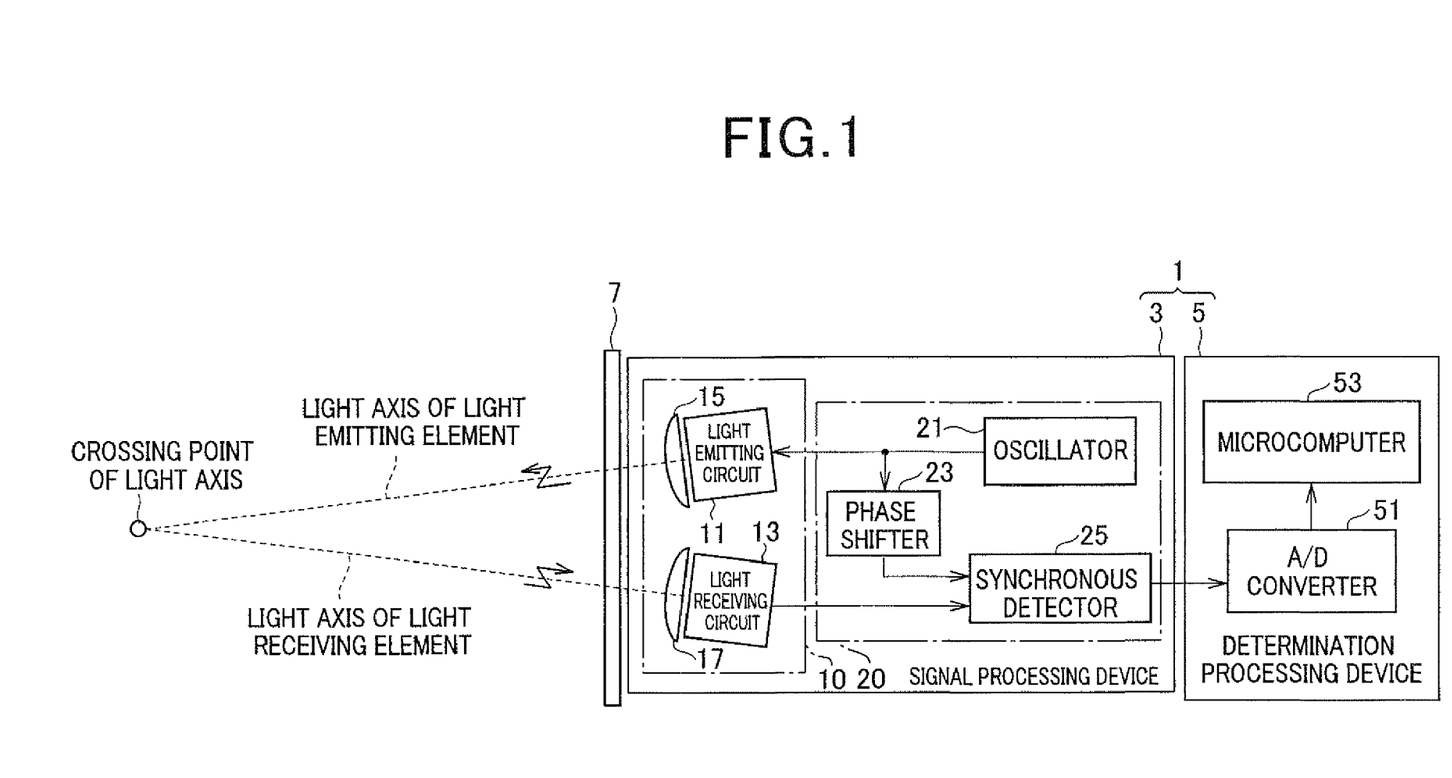
FIG. 1 is a block diagram showing a construction of a fog detector according to a first embodiment of the invention.
Figure 3A:
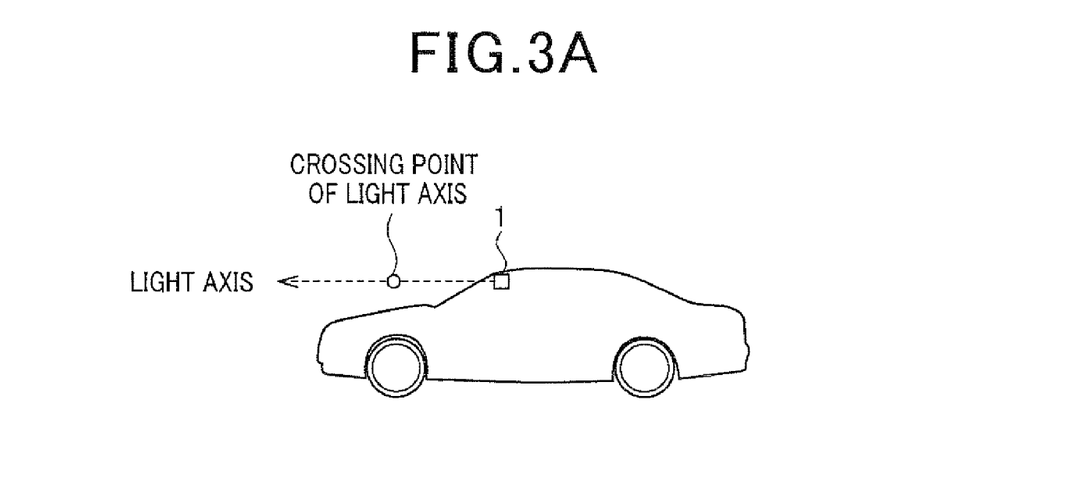
FIGS. 3A to 3C are explanatory drawings showing a placement of the fog detector and conditions of signal reception.
Figure 3B:
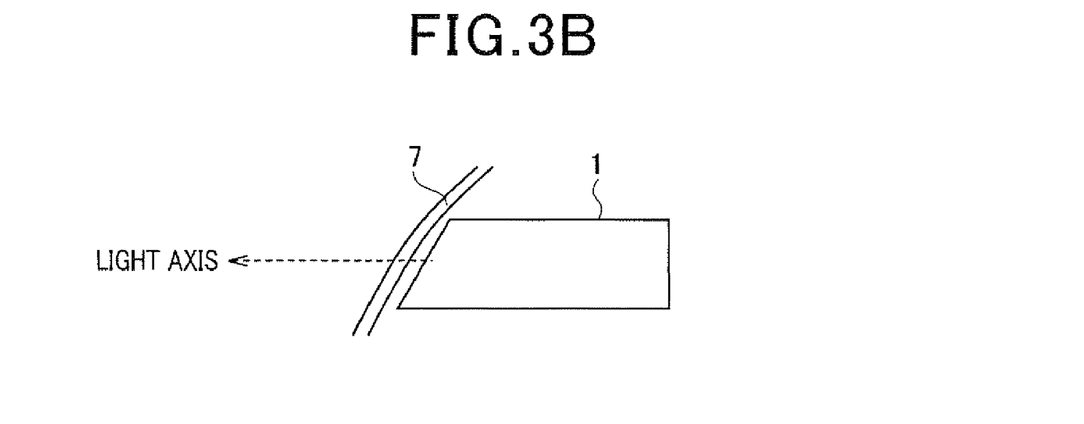
Figure 3C:
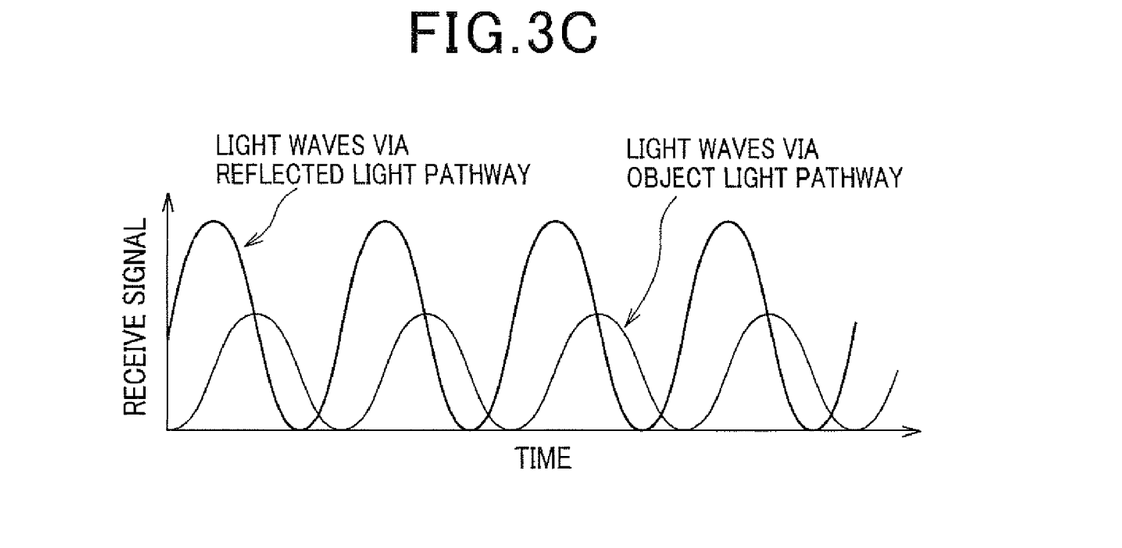

FIG. 1 is a block diagram showing a full construction of a fog detector 1 according to a first embodiment of the invention. FIG. 3 is an explanatory drawing showing the placement position of the fog detector 1.

As shown in FIG. 1, the fog detector 1 consists of a sensor device 3 and a determination processing device 5. The sensor device 3 consists of an emitting/receiving device 10 and a signal processing device 20. The emitting/receiving device 10 emits and receives light waves (infrared radiation of 900 nm, in this embodiment). The signal processing device 20 provides transmission signals to the emitting/receiving device 10 to allow the emitting/receiving device 10 to emit light waves. The signal processing device 20 also processes received signals provided from the emitting/receiving device 10 after the emitting/receiving device 10 receives the light waves. The determination processing device 5 performs a determination process based on the signals processed by the signal processing device 20 of the sensor device 3.

The emitting/receiving device 10 consists of a light emitting circuit 11, a light receiving circuit 13, a light emitting lens 15, and a light receiving lens 17. The light emitting circuit 11 is composed of a light emitting element (a light emitting diode, for example) that emits light waves, and its driving circuit. The light receiving circuit 13 is composed of a light receiving element (a photo diode, for example) and its driving circuit. The light emitting lens 15 functions to narrow down the focus of the spread dimension of outgoing light from the light emitting element to cause the spread dimension to become $2\theta_2$. The light receiving lens 17 functions to collect incoming light to cause the receiving angle of the light receiving element to become $2\theta_1$.

The light emitting element and the light receiving element are placed in such a direction that each light axis crosses with the other light axis, and that the light pathway length R1 of the pathway of the light waves (hereinafter referred to as "the object pathway"), which reach the light receiving element after emitted from the light emitting element via reflection at the crossing point of the light axes, becomes ¼ of the wavelength λ of the transmission signals.

Figure 6A:
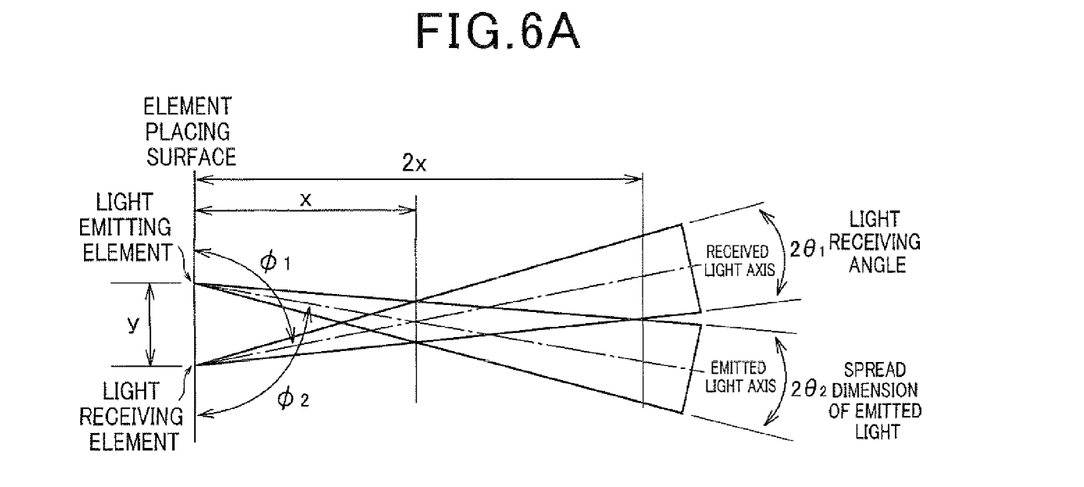
FIGS. 6A to 6B are explanatory drawings showing placement conditions of a light emitting element and a light receiving element.
Figure 6B:
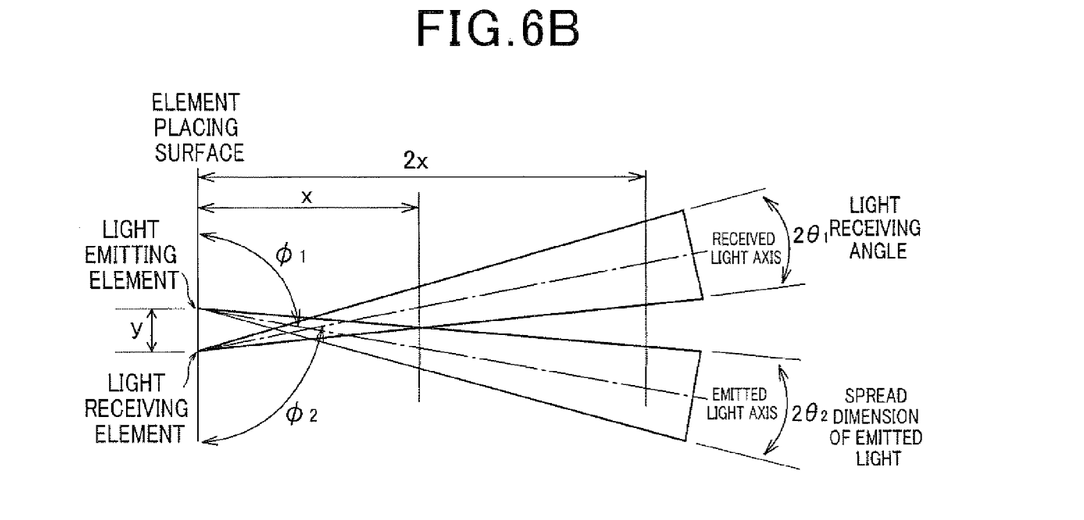

The features of the light emitting lens 15, the light receiving lens 17, and the wavelength λ of the transmission signals are determined to satisfy the following formulas (7) and (8). In the formulas, the symbol "$\phi_1$" refers to the angle of the light receiving element toward the light emitting element in the forward direction of the vehicle, and "$\phi_2$" refers to the angle of the light emitting element toward the light receiving element in the forward direction of the vehicle. Further, symbol "x" refers to the distance between an element placing surface for placing the light emitting and the light receiving elements and the crossing point of the light axes and the symbol "y" refers to a placement distance between the light emitting element and the light receiving element (see FIG. 6).

$$y < \frac{2x}{\tan(\phi_1 + \theta_1)} + \frac{2x}{\tan(\phi_2 + \theta_2)} \quad (7)$$

$$y > \frac{x}{\tan(\phi_1 + \theta_1)} + \frac{x}{\tan(\phi_2 + \theta_2)} \quad (8)$$

The signal processing device consists of an oscillator 21, a phase shifter 23, and a synchronous detector 25. The oscillator 21 generates transmission signals (for example, λ=6 m, f=50 MHz) having the wavelength λ between several dozen centimeters and several meters. The phase shifter 23 generates the reference signals by dividing and taking a part of the transmission signals, and by delaying the part of the transmission signals for the time T1 (=R1/c, in which "c" refers to the speed of light) that is needed for the light waves to move in the subject light pathway having the light pathway length R1 (=λ/4). The synchronous detector 25 selects signals synchronized with the reference signals (having the same frequency and phase) among the signals received based on the receive signals provided from the light receiving circuit 13 and the reference signals provided from the phase shifter 23, and generates detecting signals that represents the amplitude of the selected signals.

Figure 2:
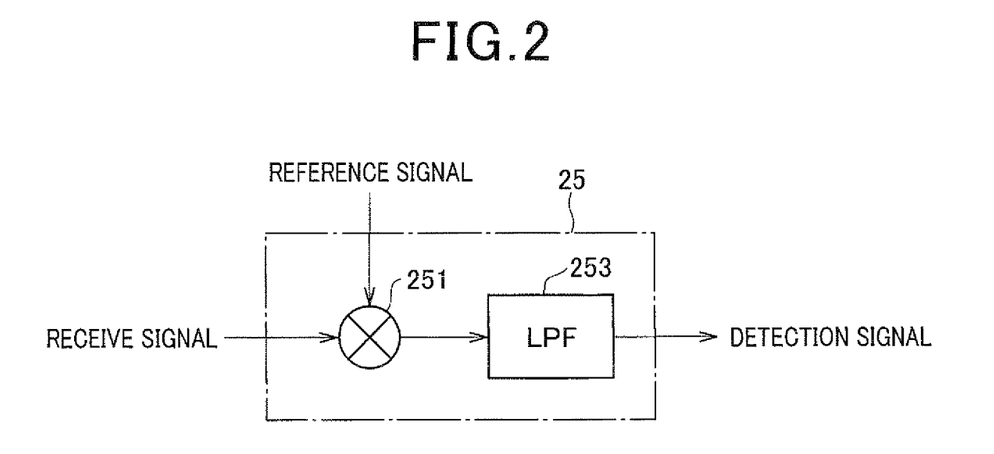
FIG. 2 is a block diagram showing a construction of a synchronous detector.

As shown in FIG. 2, the synchronous detector 25 is a well-known type having a mixer 251 that mixes the receive signals and the reference signals, and a low-pass filter (LPF) 253 that smoothes output of the mixer 251.

That is, the synchronous detector 25 is constructed to selectively detect the amplitude of the light waves that are scattered by the fog and the like in the air and reach the light receiving element through the light pathway having the light pathway length of R1, after emission from the light emitting element.

As shown in FIG. 1, the determination processing device 5 is composed of an A/D converter 51 that converts an output of the synchronous detector 25 as an analog to digital conversion, and a microcomputer 53 that performs a determination process to determine whether the fog exists or not. The particular process by the microcomputer 53 can be such that it compares the converted output data from the A/D converter 51 with predetermined threshold value to judge an existence of fog. That is, the microcomputer can calculate a density of fog based on amount of the output data (i.e., intensity of the output signal of the synchronous detector 25). A density of the fog is estimated based on the intensity of a backscattered light reflected from particles in the fog and can be used for judging the existence of the fog as described above. In the present invention, the density of fog is defined as follows.

visibility range=a/intensity of backscattered light where: "visibility range" is a maximum viewable distance due to the density of fog, and "a" is constant.

The density of fog is expressed as the "visible distance" that decreases as the density of fog (in other word, thickness of fog) increases.

As shown in FIGS. 3(a) and 3(b), the fog detector with such construction is placed in the upper part of a vehicle interior, facing the front glass 7.

The fog detector 1 is placed at a position that is satisfied by the following formula (9). In this formula, the symbol "ΔR (=R1−R2)" refers to the length difference of the light pathways between the object light pathway and the reflected light pathway, where the symbol "R2" refers to the length of the pathway of the light waves (hereinafter, referred to as "the reflected light pathway") that are emitted from the light emitting element constructing the light emitting circuit 11, and is received by the light receiving element constructing the light receiving circuit 13, through reflection at the front glass 7.

$$\Delta R = \lambda/4 \tag{9}$$

That is, as shown in FIG. 3(*c*), the light waves received via the object pathway is arranged to delay by $\pi/2$ in the phase from the light waves received via the reflected light pathway.

When the emitted light from the light emitting circuit 11 is represented by "sin ωt", the received light waves (the reflected light from the front glass) via the reflected light pathway is represented by "$A1 \cdot \sin(\omega t + \phi)$", and the received light waves via the object pathway (the backscattered light from the fog present at the crossing point of the light axes) is represented by "$A2 \cdot \sin(\omega t + \phi + \pi/2)$". The received signals provided from the light receiving circuit 13 to the synchronous detector 25 are represented by the formula (10).

$$A1 \cdot \sin(\omega t + \phi) + A2 \cdot \sin(\omega t + \phi + \pi/2) \tag{10}$$

Further, the reference signal from the phase shifter 23 is represented by "$A3 \cdot \sin(\omega t + \phi + \pi/2)$". Then, the alternating current (AC) component is removed from a mixed signal represented by multiplying (mixing) the formula "$A3 \cdot \sin(\omega t + \phi + \pi/2)$" by the formula (10). As a result, the synchronous detector 25 completes extraction of a signal that is proportional to the amplitude of the light waves A2 via the object light pathway.

As described hereinabove, the fog detector 1 is constructed by setting the light pathway length R1, R2 of both of the light waves such that the object light, which is the light waves move via the object light pathway (the backscattered light from the fog present at the crossing point of the light axes), delayed by $\pi/2$ in the phase from the reflected light, which is the light waves move via the reflected light pathway (the reflected light from the front glass). Further, the synchronous detector 25 is constructed to extract signals having the same phase as the object light waves.

Accordingly, the fog detector 1 can detect the object light without being influenced by the reflected light, which allows the determination processing device 5 to accurately determine the density of fog.

Further, the fog detector 1 is constructed to allow the light waves to be present in the cross area, whose light pathway from the light emitting element to the light receiving element through reflection by the fog is equal to the wave length of the light waves. But, it is constructed not to allow the light waves to be present in the cross area, whose light pathway is two times longer than the length of the light waves (see, formulas (7) and (8)). The cross area is a zone where the area having the spread dimension of $2\theta_1$ about the light axis of the light receiving element (received light axis) and the area having the spread dimension of $2\theta_2$ about the light axis of the light emitting element (emitted light axis) cross each other.

Accordingly, the fog detector 1 does not allow the light receiving circuit 13 to receive light waves having the same phase as the reference signals, except the light waves whose light pathway is R1, thereby improving the reliability in detection.

Further, a window glass 7 through which the emitted light from the fog detector 1 and the object light to be received by the detector 1 penetrate is generally equipped with a wiper, which allows the detector 1 to keep itself in a good condition with little reflected light to be received, with minimum effort.

The fog detector 1 in the embodiment determines the positional relationship between the fog detector 1 and the front glass 7 based on the predetermined condition such as the placement angles $\phi_1$, $\phi_2$ of the light receiving element and the light emitting element, respectively, the placement distance "y", the light receiving angle $\theta_1$, the spread dimension of the emitted light $\theta_2$, and the wavelength $\lambda$ of the transmission signals. Contrary to this, the feature of the fog detector 1 can be designed based on the predetermined positional relationship between the fog detector 1 and the front glass 7.

Further, the fog detector 1 in this embodiment has been designed such that the length difference of the light pathway length $\Delta R$ (=R1−R2) between the object light pathway and the reflected light pathway becomes ¼ of the wavelength $\lambda$ of the transmission signals, and based on this, the phase is delayed by $\pi/2$ in the phase shifter 23. The fog detector 1, however, can be designed such that the length difference of the light pathway length $\Delta R$ becomes equal to the wavelength of the transmission signals. Hence, the phase shifter 23 can be omitted.

Second Embodiment

A second preferred embodiment of the invention will be described hereinafter.

Figure 4:
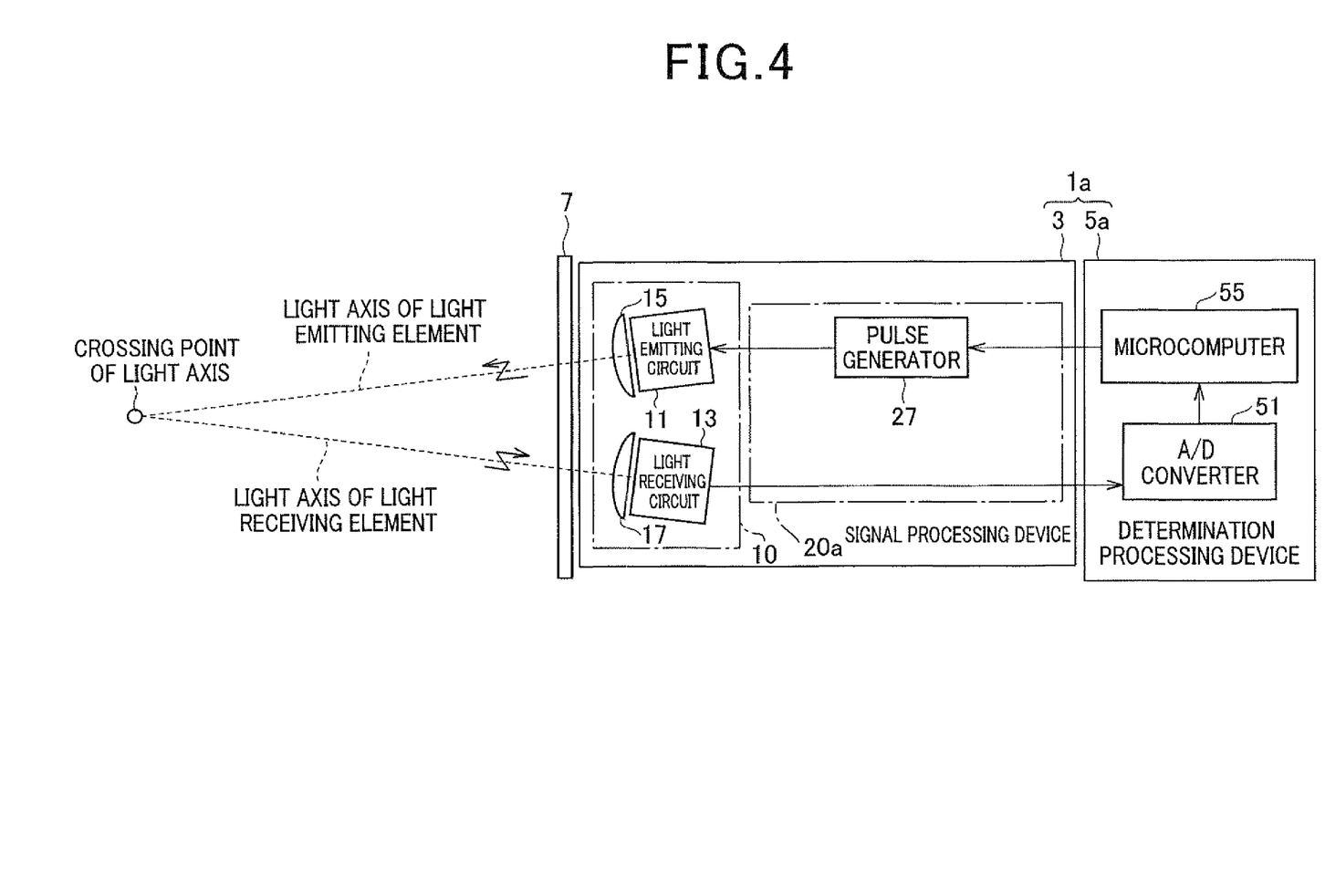
FIG. 4 is a block diagram showing a construction of a fog detector according to a second embodiment of the invention.
Figure 5:
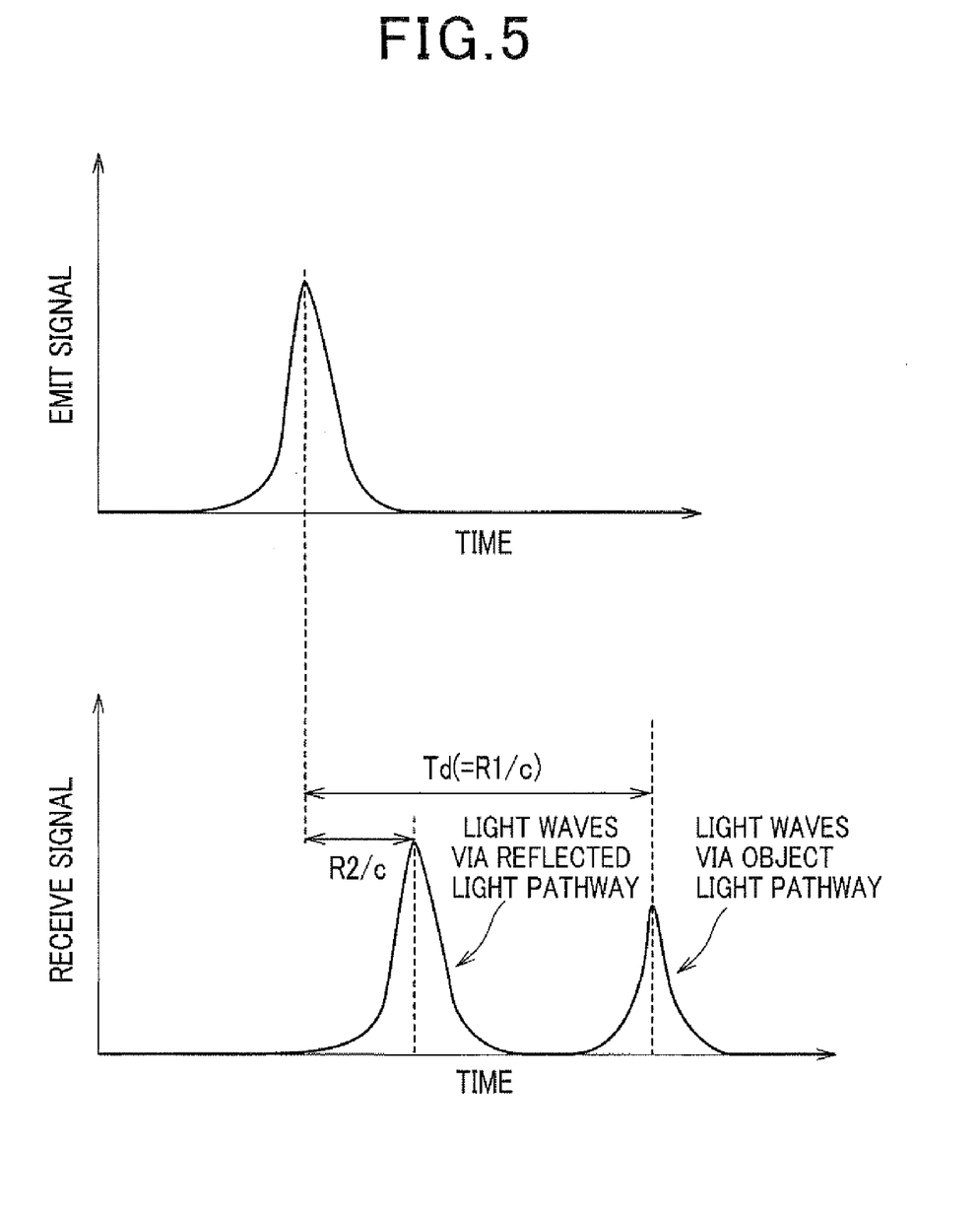
FIG. 5 is an explanatory drawing showing the time difference between received signals.

FIG. 4 is a block diagram showing the construction of a fog detector 1*a* according to the embodiment.

The fog detector 1*a* includes an emitting/receiving device 10 having the same construction as that of the fog detector 1 in the first embodiment. In the fog detector 1*a*, only such conditions are dissimilar with those in the fog detector 1 in the first embodiment are the placement position of the emitting/receiving device 10, the feature of lenses 15, 17 constructing the emitting/receiving device 10, the construction of the signal processing device 20, and the processing content of the determination processing device 5. Therefore, the devices dissimilar with the first embodiment in the same structures will be primarily described.

The emitting/receiving device 10 is placed in such a manner that the light axis of a light emitting element constructing a light emitting circuit 11 and the light axis of a light receiving element constructing a receiving circuit 13 cross each other. Accordingly, the light pathway length R1 of the pathway of the light waves (object light pathway) is determined, which are emitted from the light emitting element and received by the light receiving element via the crossing point of the axes.

The signal processing device 20*a* is composed of a generator 27 that generates pulse-like transmission signals having the pulse width of Tp, by following the start-up order from the determination processing device 5. The determination processing device 5*a* consists of an A/D converter 51 and a microcomputer 55. The microcomputer 55 outputs the start-up order to the pulse generator 27. The microcomputer 55 also completes process of determination of the fog density like the first embodiment, based on the A/D converted data by the A/D converter 51 converted at least during the time equal to the pulse width Tp starting from the timing delayed for the time Td (=R1/c) in which the light waves via the object light pathway reach the light receiving element.

The fog detector 1*a* constructed as such is placed at an upper part of the vehicle interior to face a front glass 7, like the first embodiment.

The fog detector 1*a* is placed in a position that is satisfied by the following formula, in which "R2" refers to the light pathway length of the pathway of the light waves (that is, the reflected light pathway) that reach the light receiving element after emitted from the light emitting element via reflection at the front glass.

$$(R1 - R2)/c > Tp \tag{11}$$

That is, as shown in FIG. 6, the fog detector 1a is placed in such a manner that the light waves received via the object light pathway and the light waves received via the reflected light pathway do not overlap each other.

As described above, the fog detector 1a receives the light waves (object light) via the object light pathway and the light waves (reflected light) via the reflected light pathway at different timings, where both of the light waves do not overlap each other. Further, the fog detector 1a determines the density of fog using the A/D converted data provided at the timing that the object light is received.

Accordingly, the fog detector 1a can detect the object light of the reflected light, resulting in sufficient determination of the fog density.

In this embodiment, the placement relationship of the front glass 7 and the fog detector 1a is determined based on the predetermined directions of the light receiving element and the light emitting element φ1, φ2. Contrary to such arrangement, the directions of the light receiving element and the light emitting element φ1, φ2 as well as the pulse width Tp of the transmission signals can be determined based on the predetermined placement relationship between the front glass 7 and the fog detector 1a.

Other Embodiments

Although the fog detectors 1, 1a in the above-mentioned embodiments combine all the devices in one unit, the sensor device 3, and the determination processing devices 5, 5a can be separated. Further, each of the emitting/receiving device 10 and the signal processing devices 20, 20a can be constructed individually, and only the sensor device 3, or only the emitting/receiving device 10 can be placed against the window glass 7.

Further, the fog detectors 1, 1a in the embodiments are placed by the front glass 7, the protective wall, they can be placed by a rear glass or other window glasses as well as by a glass constructing a head light.

In such cases, those glasses should be equipped with a wiper that removes drops of water adhered to the glasses.

While the present invention has been disclosed in terms of the preferred embodiment in order to facilitate better understanding thereof, it should be appreciated that the invention can be embodied in various ways without departing from the principle of the invention.

What is claimed is:

1. A fog detector placed in a vehicle interior that is segregated from an exterior by a translucent protective wall, the fog detector comprising:
an emitting/receiving device that includes a light emitting element for emitting light waves and a light receiving element for receiving light waves, wherein the light emitting element and the light receiving element are placed in such a manner that the light axes of the elements cross at a crossing point of the light axes;
a signal processing device that provides a transmission signal having a predetermined frequency to the light emitting element for emitting the light waves and performs a synchronous detection of a received signal corresponding to the received light waves provided from the light receiving element so as to extract a signal corresponding to a reflected light waves reflected from the crossing point of the light axes, wherein the synchronous detection is performed using a reference signal having the same frequency as the transmission signal and the same phase as the reflected light waves reflected from the crossing point of the light axes; and
a determination processing device that determines whether or not fog exists based on results of the synchronous detection performed by the signal processing device,
wherein the light emitting element and the light receiving element have a characteristic such that a light receiving angle $2\theta_1$ of the light receiving element and a spread dimension $2\theta_2$ of the emitted light from the light emitting element satisfy the following formula:

$$y < \frac{2x}{\tan(\phi_1 + \theta_1)} + \frac{2x}{\tan(\phi_2 + \theta_2)}$$
$$y > \frac{x}{\tan(\phi_1 + \theta_1)} + \frac{x}{\tan(\phi_2 + \theta_2)}$$

where "x" refers to the linear distance between an element placing surface and the crossing point of the light axes, the light emitting element and the light receiving element being placed on the element placing surface, "$\phi_1$" refers to a light axis angle of the light receiving element relative to the element placing surface, "$\phi_2$" refers to a light axis angle of the light emitting element relative to the element placing surface, and "y" refers to a placement distance between the light emitting element and the light receiving element.

2. The fog detector according to claim 1, wherein the determination processing device estimates a fog density based on the intensity of the signal corresponding to the reflected light waves reflected at the crossing point of the light axes, and determines whether or not fog exists by comparing fog density with a predetermined value.

3. The fog detector according to claim 1, wherein the emitting/receiving device is placed in such a manner that the light axes of the emitting/receiving device pass through the protective wall, the crossing point of the light axes is provided at the exterior of the vehicle, the difference distance between a light pathway length of light waves that roundtrip the crossing point of the light axes and a light pathway length of light waves that reflect at the protective wall is $\Delta R$; in such condition the wavelength of the transmission signals $\lambda$, satisfies the following formula:

$$\Delta R = \lambda/4.$$

4. A fog detector placed in a vehicle interior that is segregated from an exterior by a translucent protective wall, the fog detector comprising:
an emitting/receiving device, the emitting/receiving device includes a light emitting element and a light receiving element, the light emitting element and the light receiving element are placed in such a manner that the light axes of the elements cross each other;
a signal processing device, the signal processing device provides transmission signals having predetermined pulse width to the light emitting element, the signal processing device being arranged to detects a signal level of the received signals provided from the light receiving element, and
a determination processing device that determines the density of fog based on detected signals detected by the signal processing device, wherein the detected signals are detected at a timing delayed from the transmission signals for the time that is needed for the emitted light from the light emitting element to reach the light receiving element via reflection at a crossing point of the light axes,
wherein the emitting/receiving device is placed in such a manner that the light axes of the emitting/receiving device pass through the protective wall, the crossing point of the light axes is provided at an exterior of the vehicle, a difference distance between a light pathway length of light waves that roundtrip the crossing point of the light axes and a light pathway length of light waves that reflects at the protective wall is ΔR; in such condition a pulse width "Tp" of the transmission signals satisfies the following formula, in which "c" is the speed of light:

ΔR/c>Tp.

5. A placement method of the fog detector disclosed in claim 1, comprising:
placing the emitting/receiving device in such a manner that the light axes of the emitting/receiving device pass through the protective wall;
having a crossing point of the light axes at an exterior of the vehicle; and
having the placement position of the emitting/receiving devices satisfy the following formula, in which "ΔR" refers to a difference distance between a light pathway length of light waves that roundtrip the crossing point of the light axes and a light pathway length of light waves that reflect at the protective wall, and "λ" refers to the wavelength of the transmission signals:

ΔR=λ/4.

6. A placement method of the fog detector disclosed in claim 4, comprising:
placing the emitting/receiving device in such a manner that the light axes of the emitting/receiving device pass through the protective wall;
having a crossing point of the light axes at an exterior of the vehicle; and
having the placement position of the emitting/receiving devices satisfy the following formula, in which "ΔR" refers to the distance difference between a light pathway length of light waves that roundtrip the crossing point of the light axes and a light pathway length of light waves that reflect at the protective wall, "c" refers to a speed of light, and "Tp" refers to a pulse width of the transmission signals:

ΔR/c>Tp.

7. The placement method of the fog detector disclosed in claim 5, wherein the protective wall is provided with a wiper for removing drops of water adhered to the protective wall.

8. The placement method of the fog detector disclosed in claim 5, wherein the protective wall is a front windshield or a rear windshield.

9. A fog detector placed in a vehicle interior that is segregated from an exterior by a translucent protective wall, the fog detector comprising:
an emitting/receiving device that includes a light emitting element for emitting a light waves and a light receiving element for receiving light waves, wherein the light emitting element and the light receiving element are placed in such a manner that the light axes of the elements crosses at a crossing point of the light axes;
a signal processing device that provides a transmission signal having a predetermined frequency to the light emitting element for emitting the light waves and performs a synchronous detection of a received signal corresponding to the received light waves provided from the light receiving element so as to extract a signal corresponding to a reflected light waves reflected from the crossing point of the light axes, wherein the synchronous detection is performed using a reference signal having the same frequency as the transmission signal and the same phase as the reflected light waves reflected from the crossing point of the light axes; and
a determination processing device that determines whether or not fog exists based on results of the synchronous detection performed by the signal processing device
wherein the emitting/receiving device is placed in such a manner that the light axes of the emitting/receiving device pass through the protective wall, the crossing point of the light axes is provided at the exterior of the vehicle, the difference distance between a light pathway length of light waves that roundtrip the crossing point of the light axes and a light pathway length of light waves that reflect at the protective wall is ΔR; in such condition the wavelength of the transmission signals λ satisfies the following formula:

ΔR=λ/4.

10. A placement method of a fog detector placed in a vehicle interior that is segregated from an exterior by a translucent protective wall, the fog detector having:
an emitting/receiving device that includes a light emitting element for emitting light waves and a light receiving element for receiving light waves, wherein the light emitting element and the light receiving element are placed in such a manner that the light axes of the elements cross at a crossing point of the light axes;
a signal processing device that provides a transmission signal having a predetermined frequency to the light emitting element for emitting the light waves and performs a synchronous detection of a received signal corresponding to the received light waves provided from the light receiving element so as to extract a signal corresponding to a reflected light waves reflected from the crossing point of the light axes, wherein the synchronous detection is performed using a reference signal having the same frequency as the transmission signal and the same phase as the reflected light waves reflected from the crossing point of the light axes; and
a determination processing device that determines whether or not fog exists based on results of the synchronous detection performed by the signal processing device
wherein the method comprises:
placing the emitting/receiving device in such a manner that the light axes of the emitting/receiving device pass through the protective wall;
having a crossing point of the light axes at an exterior of the vehicle; and
having the placement position of the emitting/receiving devices satisfy the following formula, in which "ΔR" refers to a difference distance between a light pathway length of light waves that roundtrip the crossing point of the light axes and a light pathway length of light waves that reflect at the protective wall, and "λ," refers to the wavelength of the transmission signals:

ΔR=λ/4.

11. The placement method of the fog detector disclosed in claim 10, wherein the protective wall is provided with a wiper for removing drops of water adhered to the protective wall.

12. The placement method of the fog detector disclosed in claim 10, wherein the protective wall is a front windshield or a rear windshield.

* * * * *